(12) United States Patent
Menne et al.

(10) Patent No.: US 10,806,721 B2
(45) Date of Patent: Oct. 20, 2020

(54) FORMULATION FOR USE IN THE TREATMENT OF UREMIC PRURITUS

(71) Applicant: DRUG DELIVERY SOLUTIONS, Hoersholm (DK)

(72) Inventors: Torkil Menne, Hoersholm (DK); Johan Selmer, Hoersholm (DK); Jesper Lange, Hoersholm (DK); Michelle Georgiou, Leatherhead (GB); Derek Wheeler, Leatherhead (GB); David Evans, Leatherhead (GB)

(73) Assignee: DRUG DELIVERY SOLUTIONS APS, Hoersholm (DK)

( * ) Notice: Subject to any disclaimer, the term of this patent is extended or adjusted under 35 U.S.C. 154(b) by 0 days.

(21) Appl. No.: 16/310,025

(22) PCT Filed: Jun. 16, 2017

(86) PCT No.: PCT/DK2017/050201
§ 371 (c)(1),
(2) Date: Dec. 14, 2018

(87) PCT Pub. No.: WO2017/215723
PCT Pub. Date: Dec. 21, 2017

(65) Prior Publication Data
US 2019/0321336 A1 Oct. 24, 2019

(30) Foreign Application Priority Data

Jun. 17, 2016 (DK) .................................. 2016 70438
Mar. 28, 2017 (DK) .................................. 2017 70225

(51) Int. Cl.
*A61K 31/4164* (2006.01)
*A61K 31/4172* (2006.01)
*A61P 17/04* (2006.01)
*A61K 9/00* (2006.01)
*A61K 9/107* (2006.01)
*A61K 31/4015* (2006.01)

(52) U.S. Cl.
CPC ........ *A61K 31/4172* (2013.01); *A61K 9/0014* (2013.01); *A61K 9/107* (2013.01); *A61K 31/4015* (2013.01); *A61P 17/04* (2018.01)

(58) Field of Classification Search
CPC .................................................. A61K 31/4164
USPC ........................................................ 514/400
See application file for complete search history.

(56) References Cited

U.S. PATENT DOCUMENTS

| 4,025,645 | A | 5/1977 | Jelenko, III |
| 5,811,446 | A | 9/1998 | Thomas |
| 6,573,302 | B1 | 6/2003 | Holt et al. |
| 2009/0017129 | A1 | 1/2009 | Ma'or et al. |
| 2009/0186853 | A1 | 7/2009 | Yu et al. |
| 2011/0217227 | A1 | 9/2011 | Engsl et al. |
| 2012/0230929 | A1 | 9/2012 | Nieuwenhuijsen |
| 2014/0178458 | A1* | 6/2014 | Smola .............. A61Q 19/00 424/443 |
| 2014/0377338 | A1 | 12/2014 | Morariu |
| 2015/0252035 | A1 | 9/2015 | Liedtke et al. |
| 2016/0008297 | A1 | 1/2016 | Schmaus et al. |

FOREIGN PATENT DOCUMENTS

WO 2009/103959 A2 8/2009

OTHER PUBLICATIONS

International Search Report and Written Opinion from International Application No. PCT/DK2017/050201, dated Sep. 19, 2017.
George R. Stark "Reactions of Cyanate with Functional Groups of Proteins. III. Reactions with Amino and Carboxyl Groups", Biochemistry.
Berg et al., "Carbamylation of Serum Albumin as a Risk Factor for Mortality in Patients with Kidney Failure", Sci Transl Med. Mar. 6, 2013; 5(175): 175ra29. doi:10.1126/scitranslmed.3005218.

* cited by examiner

*Primary Examiner* — Raymond J Henley, III
(74) *Attorney, Agent, or Firm* — Merchant & Gould P.C.

(57) ABSTRACT

There is provided a topical formulation comprising a nucleophile, such as amino acids and most polypeptides and/or a derivative thereof, for use in the treatment or prevention of itchy dry skin caused by urea, such as in uremic pruritus, of a subject. The amino acid may be histidine and the derivative may be a histidine degradation product, a peptide of histidine, a peptide of histidine and one or more additional amino acids, and a pharmaceutically-acceptable salt of histidine.

15 Claims, 4 Drawing Sheets

Day 3

Control

Carbamid crème 5%

Carbamid crème 10%

Urea 6 mg

Urea 12 mg

Urea 12 mg + 10 mg His

Day 6

Control

Carbamid crème 5%

Carbamid crème 10%

Urea 6 mg

Urea 12 mg

Urea 12 mg + 10 mg His

Day 6

GM (control)

GM + 4mg urea

GM + 4 mg urea + creame

FORMULATION FOR USE IN THE TREATMENT OF UREMIC PRURITUS

This application is a National Stage Application of PCT/DK2017/050201, filed 16 Jun. 2017, which claims benefit of Serial No. PA 2017 70225, filed 28 Mar. 2017 in Denmark and Serial No. PA 2016 70438, filed 17 Jun. 2016 in Denmark, and which applications are incorporated herein by reference. To the extent appropriate, a claim of priority is made to each of the above disclosed applications.

FIELD OF INVENTION

The present invention relates to a topical formulation comprising a nucleophilic compound, such as histidine or any other amino acids or polypeptides and/or a derivative thereof, for use in the treatment of itchy dry skin caused by urea, such as in uremic pruritus, of a subject. The present invention also relates to a topical composition for use in the prevention uremic pruritus.

BACKGROUND FOR INVENTION

Uremic pruritus is one of the most distressing symptoms of renal failure. It affects up to 50% of patients in dialysis (I). The skin of the uremic patients is often pale, due to anemia, dry and with scratch marks. The condition may include skin symptoms such as eczema, prurigo nodularis, nummular eczema and licinification. The subjective symptoms include intense itching and burning which may be localized or generalized. There have been many hypothesis for the etiology of the condition which have led to a number of systemic and topical treatments. In general these treatments have little or no effect although some may help in subgroups of patients (I).

Metabolic and endocrine changes in uremic dialyzed patients are many and complex (2). The accumulation of urea in the body is one of the central metabolic changes in chronic renal disease. Urea is excreted both via the renal system and through the sweat (3). The concentration in sweat is 2-4 times higher than the serum concentration. This implies that high concentrations of urea can be present on the skin in uremic patients (4). Sometimes the concentration is so large that urea is visible as uremic frost.

The stratum corneum, the outer part of the skin, is composed of layers of keratinized epithelia, in the form of protein enriched corneocytes, embedded in a lipid intercellular matrix composed of ceramides, cholesterol and free fatty acids and mixed with natural moisturizing factors (NMFs) (5) (6). Fifty percent of the NMF is composed of amino acids resulting from the enzymatic break down of epidermal proteins particularly filaggrin (6), and its pivotal amino acid degradation products including histidine, trans-urocanic acid and pyrrolidone carboxylic acid (7). The remaining part of the NMF is consists of components of sweat including electrolytes, lactic acid, urea, and to a minor extent amino acids. Beside having a moisturizing effect (water binding) the amino acids represent part of natural UV protection (trans urocanic acid) and function as a pH stabilizing factor.

Individuals with truncation mutations in the gene coding for filaggrin are strongly predisposed to a severe form of dry skin, ichthyosis vulgaris, and/or eczema. It has been shown that almost 50% of all severe cases of eczema may have at least one mutated filaggrin gene. The barrier defect seen in filaggrin null carriers also appears to lead to increased asthma susceptibility and exacerbations.

Urea has for long time been used for its ability to denature proteins both in biochemical research and in industrial processes (8). The denaturing action of urea on globular proteins is due to the stabilization of the unfolded form of the protein molecule. Urea also has a direct concentration dependent effect on amino acids at room temperature (8). Small amounts of cyanate which will be present in aqueous urea can add to the —NH2 groups of proteins and amino acids as well as to —SH groups present to yield carbamyl derivatives (9). It has been demonstrated that the logarithm of the rate constant for reaction between cyanate and amino acids are related linearly to the PKa value of the amino groups of the amino acids or polypeptides (15).

The high concentration of urea in the stratum corneum in the uremic patient (urea coming from sweat) is therefore expected to have a profound impact on the on enzymic biological processes in the epidermis and stratum corneum. These effects have not been investigated as an etiological factor for uremic pruritus or seen as a new avenue for treatment of the condition. The denaturizing effects of urea, in the concentrations present in uremic patients, is expected to have a profound effect on the formation of the NMF. Denaturation of proteins (particularly filaggrin) must be expected to decrease the filaggrin derived amino acids that constitutes the majority of the NMF in stratum corneum. Furthermore any available histidine will not be transformed to trans-urocanic acid because the needed enzyme (histidinase) may also be denatured by the high urea concentration in the skin of the uremic patients. Histidine itself will be changed by the direct action of urea on the molecule. These disturbances, which are expected to significantly affect the quantity and quality of the NMF, have not been investigated previously because the knowledge and dynamics of the formation and biological effects of the NMF is new.

Concerning the prior art U.S. 2016/0008297 discloses a topical formulation for use in the treatment or prevention of itchy skin associated with renal diseases. There is no disclosure of a nucleophilic attack for sequestering urea, and the amino acids used in the formulation are not included to act as nucleophiles.

U.S. 20150252035 mentions treatment of itch associated with uremic pruritus among several other skin disorders but the disclosed TRPV4 inhibitors cannot sequester urea by acting as nucleophiles.

U.S. 2009/0186853 discloses a histidine derivative and N-propanoyl derivatives of amino acids that may treat pruritus. However, there is no disclosure of treating itchy dry skin caused by sequestering urea with a nucleophile. On the contrary U.S. 2009/0186853 mentions that urea may be included in the formulations.

SUMMARY OF THE INVENTION

According to the present invention, there is provided a formulation comprising a nucleophilic compound, preferably amino acids or polypeptides and/or a derivative thereof having a low amino group PKa for use in the treatment of uremic pruritus. Without being bound by any theory the present inventors have found that the undesired effects of excess urea accumulating on the skin of patients with uremic pruritus can be counteracted by the presence of nucleophilic compounds, such as nucleophilic amino acids or polypeptides and/or a derivative, such as histidine, cysteine, arginine, lysine, glycylglycine, glycylalanine or tri- or tetraglycine.

According to the analytical chemistry performed by the inventors it appears that such nucleophiles react with the urea derived cyanate and produce carbamylated end products and ammonia. Any remaining non-reacting nucleophilic amino acids, and especially histidine, exert the beneficial skin effects known from such amino acids, whereby the skin of patients with uremic pruritus is returned to a normal status without itching spots. For further details about how peptides and proteins are carbamylated reference is made to the article authored by G. R. Stark (15), which is herewith incorporated by reference.

According to the present invention, there is also provided a method for treating uremic pruritus, which method comprises administering to said subject a therapeutically effective amount of a nucleophilic compound, such as a nucleophilic amino acid, preferably histidine and/or a derivative thereof.

In another embodiment, the present invention further comprises treatment of additional skin conditions caused by presence of urea or urine, including but not limited to urostomi dermatitis, incontinence dermatitis, and diaper dermatitis, by a method comprising administering to said subject a therapeutically effective amount of a nucleophilic compound, such as a nucleophilic nucleophilic amino acids or polypeptides and/or a derivative thereof.

Specifically there is provided a topical formulation comprising histidine and/or a derivative thereof for use in the treatment or prevention of uremic pruritus of a subject, wherein the formulation is applied to the skin with a concentration of amino acids or polypeptides f and/or a derivative thereof ranging between 0.001 mg/cm$^2$ and 5 mg/cm$^2$ skin surface, preferably between 0.003 mg/cm$^2$ and 1 mg/cm$^2$ skin surface, more preferably 0.005 mg/cm$^2$ and 0.5 mg/cm$^2$ skin surface.

Preferably, the derivative is selected from amino acids or polypeptides and/or a derivative thereof having a low PKa, one or more histidine degradation products, such as trans urocanic acid, a peptide of histidine or a peptide of histidine and one or more additional amino acids, and a pharmaceutically-acceptable salt of histidine. It is preferred that the histidine is L-histidine.

In one embodiment the histidine and/or the derivative thereof is the only active ingredient in the pharmaceutical composition.

In another embodiment the formulation further comprises pyrrolidone carboxylic acid or salt thereof, preferably the sodium salt.

DETAILED DESCRIPTION OF THE INVENTION

Figure 1:
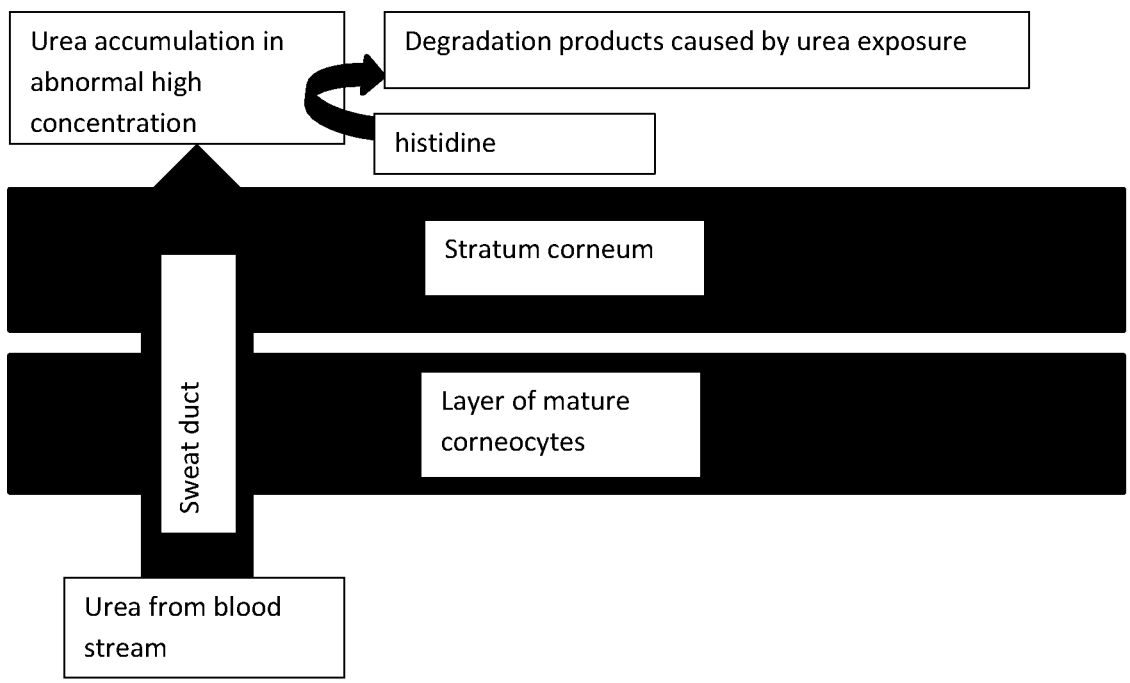
FIG. 1 shows a diagram of the biochemical disturbances associated with uremic pruritus.

As stated the present invention also provides a therapeutic method for treating uremic pruritus. Specifically the invention in its second aspect provides a method for treating uremic pruritus of a subject, wherein a topical formulation comprising histidine and/or a derivative thereof, such as trans urocanic acid (UCA), is applied to the skin with a concentration of histidine and/or a derivative thereof ranging between 0.001 mg/cm$^2$ and 5 mg/cm$^2$ skin surface, preferably between 0.003 mg/cm$^2$ and 1 mg/cm$^2$ skin surface, more preferably 0.005 mg/cm$^2$ and 0.5 mg/cm$^2$ skin surface. The amino acids or polypeptides and/or the derivative thereof may be the only active ingredient in the pharmaceutical composition. Alternatively, the formulation comprises further actives, such as pyrrolidone carboxylic acid.

The uremic pruritus is a well-defined indication, which can be clearly distinguished from inflammatory skin diseases (particularly a chronic inflammatory skin disease), such as atopic dermatitis, all types of psoriasis (including plaque flexural, guttate, pustular, nail, photosensitive, erythrodermic psoriasis and psoriatic arthritis), acne, ichthyosis, contact dermatitis, eczema, photodermatoses and dry skin disorders.

Skin barrier function is controlled by many factors, including the proteins present and the environment in which they reside (for example the pH). The inventors have realized that histidine will not be transformed to trans-urocanic acid because the needed enzyme (histidinase) may be denatured by the high urea concentration in the skin of the uremic patients.

In normal skin many proteins involved in barrier formation are pH dependent and are only active in the UCA-created acidic environment of the upper epidermis/stratum corneum (10). In addition to maintaining this homeostasis, the lowered pH of the stratum corneum directly inhibits microbial infection and growth (11). It is known that defective filaggrin may result in reduced amino acid content including reduced levels of histidine in the stratum corneum, which in turn may lead to reduced levels of trans-UCA and an abnormally high pH. A higher than optimum pH in the stratum corneum is believed to reduce pH dependent lipid processing enzymes (for example β-glucocerebrosidase) and compromise barrier function and repair (12).

However, the present investigation is not concerned with solving the physiological cause of defective filaggrin in patients suffering from the skin disorders. The inventors have instead discovered that the use of amino acids including histidine or polypeptides and/or a derivative thereof as the active ingredient in the use of the present invention appears to compensate for defective filaggrin caused by the high concentration of urea in the skin of uremic pruritus patients. There currently exists no means to prevent and/or treat uremic pruritus.

Moreover, amino acids including histidine and most polypeptides and/or a derivative thereof exhibit low or no mammalian toxicity or reported side effects at conventional doses. Accordingly, the use of amino acids including histidine and polypeptides and/or a derivative thereof as the active ingredient provides advantages in use, including easy access to patients, improvement in patient compliance resulting in increasing usage of the active ingredients in wide patient populations and longer uninterrupted treatment regimens compared to alternative medicaments currently in use. Moreover, amino acids including histidine and most polypeptides and/or a derivative thereof are expected to be useful in treating the entire body surface of patients and to be effective against a wide range of skin disorders (especially inflammatory skin diseases). Preferably such skin diseases are caused by presence of urea or urine, and includes but are not limited to urostomi dermatitis, incontinence dermatitis, and diaper dermatitis, and more preferably uremic pruritus.

As shown in FIG. 1 uremic pruritus is caused by a major excess of urea transported to the upper skin surface by the sweat ducts. The novel observation made by the present inventors is that the high urea concentration is disturbing the normal function of proteins and amino acids. Moreover, the pH regulation is negatively affected by the high concentration of urea.

The amino acids including histidine and most polypeptides and/or a derivative thereof may be used as described herein in any suitable form, for example as discussed herein.

The amino acids including histidine and most polypeptides and/or a derivative thereof may be used as a sole therapy or in combination with a conventional therapy for the prevention and/or treatment of uremic pruritus. Suitable conventional therapies include treatment with steroids (for example steroids for topical administration) and/or with suitable lipids and/or with phototherapy.

The present invention further provides the topical formulation described above for use in the treatment or prevention of pruritus in aging skin of elderly people. The invention is also directed to the use of the formulation in the treatment or prevention of itchy dry skin in filaggrin defective patients.

Pharmaceutical compositions for topical administration in accordance with the present invention may for example be in the form of solutions, creams, ointments, jellies, gels, sprays, foams, powders, liposomes, or aqueous or oily solutions or suspensions. Oil-in-water emulsions, water-in-oil emulsions or polyaphrons (high internal emulsions, gel emulsions etc) are also encompassed by the present invention. Suitable excipients and carriers include, for example, peanut oil, water, ethyl cocoate, octyl cocoate, polyoxyethylenated hydrogenated castor oil, liquid paraffin, isopropanol, glycerol, propylene glycol, paraffin, celluloses, parabens, stearyl alcohol, polyethylene glycol, isopropyl myristate and phenoxyethanol.

In the case of topical application to the scalp, the pharmaceutical composition may be formulated as a shampoo or conditioner. In the case of topical application to the skin, the pharmaceutical composition may be formulated as an additive to washing and bathing products (for example bath or shower gels and creams). Such pharmaceutical compositions for topical administration may include diluents or carriers that are also suitable for use in cosmetics.

Pharmaceutical compositions for topical administration by application to the skin may include moisturisers, and sun tan lotions and creams.

A pharmaceutical composition for topical administration may be provided in any suitable dispenser.

In the case of pharmaceutical compositions for topical administration by application to the skin, the diluent or carrier should be selected so as to assist the transport of the active ingredient across the skin barrier and may need to be one capable of crossing the keratinous layer of the skin. Many methods are known for preparation of pharmaceutical compositions for topical application. For example, the active ingredient may be mixed with known carrier materials as discussed herein.

Alternatively, the skilled person will appreciate that topical administration may be achieved by means of localized injection, for example intra-dermal injection.

Typically, compositions for topical administration (such as a cream) will contain from about 0.05 w/w % to 15 w/w %, more particularly from about 0.1 to 5 w/w %, even more particularly from about 0.2 to 2 w/w % by weight of the total composition of amino acids including histidine and polypeptides and/or a derivative thereof as the active ingredient.

The pharmaceutical compositions of the invention may be obtained by conventional procedures using conventional pharmaceutical diluents or carriers, well known in the art.

Example 1

A typical cream for topical administration may contain:

| Ingredient | % |
|---|---|
| Versagel M200 (Mineral oil (and) ethylene/propylene/styrene copolymer (and) butylene/ethylene/styrene copolymer) | 8.58 |
| Isostearyl isostearate (ISIS) | 12.87 |
| Cyclomethicone | 4.29 |
| Dimethicone 350 cst | 3.96 |
| Glycerol | 3.00 |
| Laureth 4 | 0.30 |
| 2 Pyrrolidone 5 carboxylic acid (Na salt) | 0.50 |
| Histidine | 0.50 |
| Carbomer (Ultrez 10) | 0.80 |
| Citric acid | 0.10 |
| Phenoxyethanol | 1.00 |
| Polysorbate 20 | 0.075 |
| Sodium hyalauronate | 0.05 |
| Sodium hydroxide (20% solution) | q.s (~0.70) |
| Water | q.s. (~63.28) |
| | 100.00 |

The cream may be prepared as follows. In a suitable vessel (A) combine the Versagel, Isostearyl isostearate, cyclomethicone and 0.26% laureth 4 with suitable mixing. In a second vessel (B) combine the dimethicone and 0.04% laureth 4 with suitable mixing. In a third vessel (C) mix the polysorbate 20 with 7.425% water. With moderate mixing slowly add first the contents of vessel A and then the contents of vessel B into vessel C. In a fourth vessel (D) combine the glycerol, 2-pyrrolidone-5-carboxylic acid (sodium salt), citric acid, histidine, sodium hyalauronate, phenoxyethanol and 41.55% water. In a fifth vessel (E) combine the carbomer and 13.50% water. Once fully dispersed and hydrated add with stirring the contents of vessel E into vessel C, then add the contents of vessel D. Adjust the pH (if required) using the sodium hydroxide and then make up to quantity with the remaining water.

Example 2

In order to demonstrate how the histidine is degraded in the presence of urea (which is an inevitable constituent of the skin in individuals suffering from UP) the cream of Example 1 was subjected to the exposure of 5 w/w % and 10 w/w % of urea. The degradation process was followed over time and after six weeks at 40° C. only 20% histidine was left in the cream having 10 w/w % urea.

Since histidine is an essential amino acid a continuous supply thereof is required to maintain the normal function of the skin. Further, it is important because this amino acid is a precursor for UCA, which is an important buffer for the pH regulation in the skin. With respect to uremic pruritus the degradation rate of histidine is much higher than in other skin disorders, such as atopic dermatitis. Accordingly, the inventors have realized that the supply of histidine (as well as its derivatives) must be correspondingly higher in order to compensate for the degradation, whereby normal histidine levels can be achieved. With that in mind the present inventors have formulated histidine in such high concentrations (cf Example 1).

Skin barrier function is controlled by many factors, including the proteins present and the environment in which they reside. Impaired skin barrier function may be due to defective filaggrin. Furthermore, filaggrin is broken down by proteinases to release a large amount of constituent histidine residues. The histidine residues are then deaminated by histidase to form amongst others trans-urocanic acid (trans-UCA).

The present invention is believed to address the problem of defective filaggrin in patients suffering from the itching skin disorders. The histidine and/or the derivatives thereof compensate for defective filaggrin.

Example 3

To further investigate possible carbamylation in human skin in UP (Uremic Pruritus) the inventors conducted a series of studies in the reconstructed human epidermis (RHE) model. The 4 $cm^2$ large skin samples were delivered from Episkin® in 6 well plates each with a volume of 1 ml. The experiments were carried out in 18-25 days old skin samples. RHE is a standardized technology used to investigate metabolic, toxic and inflammatory reactions in the skin (13). The skin samples were developed from human epidermal stem cells. They were developed on a polycarbamate net with an underlying growth medium. The RHE contains all the different cell layers in the epidermis, including stratum corneum. The samples are kept at 37° C. in a 5% $CO_2$ atmosphere. They are handled under sterile conditions. New growth medium is added daily. The 4 $cm^2$ large skin samples were ready for use after 18 days' development; a time span similar to the normal turnover of human skin.

12 individual experiments were carried out including 2 controls. Growth media (1 ml) were replaced daily according to the standard protocol. 6 of the samples were harvested at day 3 and 6 at day 6 and immediately frozen at minus 80° C. until protein analysis. Parts of all samples were sent for histologic examination.

The following exposures (individual experiments), all from stratum corneum side of the skin sample, were made.
1. Controls: Left untreated.
2. Urea in an aqueous solution in the same amount—calculated as mg/$cm^2$ skin—, as in UP. This calculated amount corresponds to 0.3 mg/$cm^2$, based on calculation of the sum of the average serum levels of urea in uremic patients, urea from sweat, and contribution from active transport of urea into the cells in epidermis. The addition of urea is done by the addition of 200 µl of a solution of 6 mg urea/ml) to the surface of the skin samples.
3. As under above item 2 but in double amount (0.6 mg/$cm^2$).
4. As under above item 3 and added 200 µl of a 1% histidine solution.
5. 5% commercially available urea cream dosed as intended human use
6. 10% commercially available urea cream dosed as intended human use The skin samples harvested at day 3 were exposed day 0 to 2-6 and day 1 to 2-4. (tabl. 1)

The skin samples is harvested at day 6 were exposed as above and further day 3 to 2-6. In agreement with Table 1 the aqueous urea solution was absorbed immediately through the skin samples. The two creams left a deposit on top of the skin and were therefore only applied twice; day 0 and day 3 (for the 6-day experiment). Daily exposures were abstained to minimize the risk of infection. The two different application methods are therefore not directly comparable as a continuous urea exposure must be anticipated from the depot effects of the creams. Further the urea concentrations from experiments 2, 3 and 4 harvested day 6 may have been relatively low due to only one supplementary exposure day 3.

Figure 2:
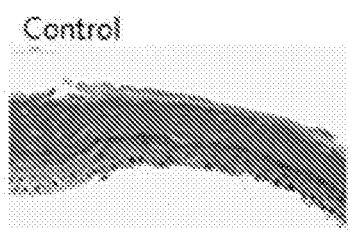
FIG. 2 shows histological examination of reconstructed human epidermis samples exposed to urea.
Figure 2:
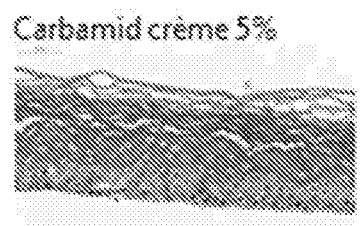
Figure 2:
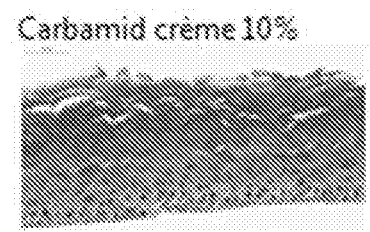
Figure 2:
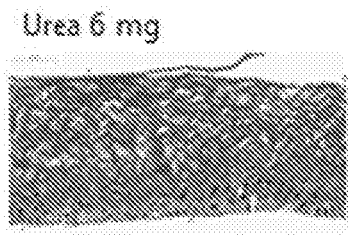
Figure 2:
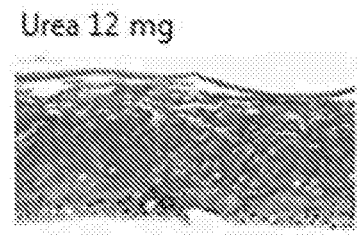
Figure 2:
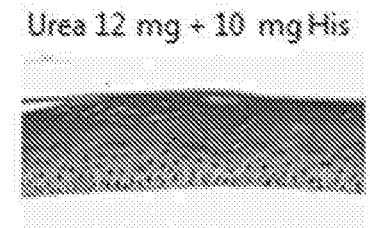
Figure 3:
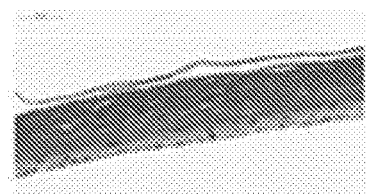
FIG. 3 shows histological examination of reconstructed human epidermis samples exposed to urea.
Figure 3:
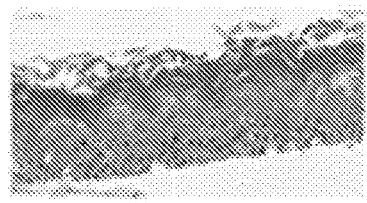
Figure 3:
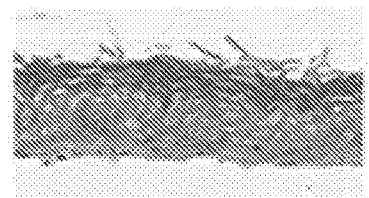
Figure 3:
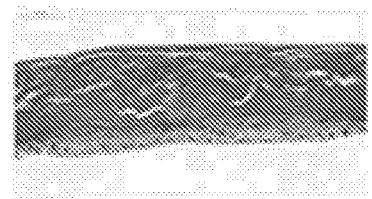
Figure 3:
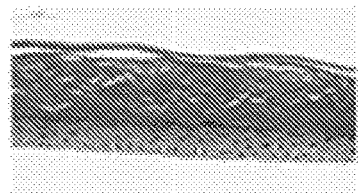
Figure 3:
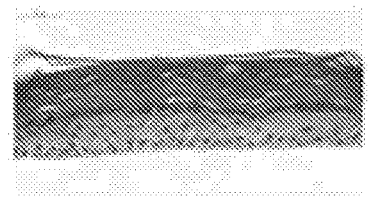

FIGS. 2 and 3 show the histological pictures for the experiments harvested day 3 and day 6. At day 3 significant changes are seen in experiments 2, 3, 5 and 6. Severe edema and disruptions are seen in the stratum corneum and premature cell death in stratum spinosum. Experiment 1 (the control) and 4 are similar and identical with the general look of 18 days old untreated RHS samples. Similar histological changes are seen in the 6 days' experiments. It is obvious that the skin samples are older. In experiment 2 and 3 the skin has recovered to a certain extent, probably reflecting the limited urea exposure (only day 3).

The experiments illustrate a likely dose and time dependent urea effect on the RHS samples. The pronounced edema of the stratum corneum reflects the water binding capacity of urea. But the cell death also point to direct toxic effect from the cyanide ion released from urea in an aqueous solution. It is remarkable that histidine, a nucleophile, can counteract this effect as illustrated in experiment 4 harvested both day 3 and day 6.

Protein analysis was made according to a previous developed method (14). Carbamoylated proteins from the skin samples were coated to ELISA wells and quantified using a using a primary polyclonal anti-homocitrullin antibody and a secondary labelled polyclonal detection antibody. The ELISA readings (absorbance units) are provided in Table 2.

Proteins from the skin samples were furthermore run in an SDS PAGE and an immunoblot were performed with a polyclonal anti-homocitrullin antibody. Results from this experiment confirmed that protein from experiment 6 resulted in a positive band demonstrating the presence of carbamoylated protein in this sample. The main conclusion from these experiments is that protein carbamylation can be demonstrated in a RHE model after 3 and 6 days' exposure to urea in concentrations comparable to urea in UP patients. The experiments illustrate effect of time and concentration. In accordance with the present invention histidine is therefore able to counteract these effects.

TABLE 1

Day 3

| | Day | | | |
|---|---|---|---|---|
| | 0 | 1 | 2 | 3 |
| Growth medium | X | X | X | |
| Urea creams | X | | | |
| Urea solutions | X | X | | |
| Harvest | | | | X |

Day 6

| | Day | | | | | | |
|---|---|---|---|---|---|---|---|
| | 0 | 1 | 2 | 3 | 4 | 5 | 6 |
| Growth medium | X | X | X | X | X | X | |
| Urea creams | X | | | X | | | |
| Urea solutions | X | X | | X | | | |
| Harvest | | | | | | | X |

TABLE 2

|  | Day 3 | Day 6 |
| --- | --- | --- |
| Controls | 0.318 | 0.395 |
| Urea conc. as in UP (moderate) 6 mg | 0.377 | 0.368 |
| Urea conc. as in UP (high) 12 mg | 0.316 | 0.475 |
| Urea conc. as in UP (high) 12 mg + 0.5% histidine | 0.312 | 0.321 |
| 5% urea cream | 0.452 | 0.557 |
| 10% urea cream | 0.423 | 0.606 |

The ELISA readings are presented as absorbance units.
UP: uremic pruritus

Example 4

The same method as described in example 3 was used. The studies were based on the use of the Human Reconstructed Epidermis (RHE) model purchased from Episkin®. Three experiments were made in duplicate including 2 controls. Growth media (1 ml) with and without additions (see below) were replaced daily accordingly to the standard protocol. In contrast to Example 3 the urea exposure was made by addition of urea to the growth medium. Experiment 1 corresponds to the two controls; experiment 2 was with growth medium with 4 mg/ml urea; experiment 3 was with growth medium with 4 mg/ml urea and with addition of 5 mg (500 µl) cream with 2% amino acids applied on top of RHE skin surface at Day 0 and Day 3. All 6 skin samples looked macroscopically healthy when they were harvested after 6 days. There were no signs of infection or necrosis. They were immediately frozen at minus 80° C. until protein analysis. Parts of all samples were sent for histological examination.

Histological Changes

The most pronounced changes were edema, particularly of the skin samples exposed to both urea and the two percentage amino acids. The cells were changed in both experiment 2 and 3, but there were more viable cells in the skin samples treated with 2% amino acids.

TABLE 3

Elisa readings presented as absorbance units. Average of two experiements.

| Controls GM | 0.53 |
| --- | --- |
| GM + 4 mg urea/ml | 0.68 |
| GM + 4 mg urea/ml with 2% amino acid cream on top applied Day 0 and Day 3 | 0.44 |

Protein Carbamylation

Protein carbamoylated was investigated using the same method as in Experiment 3. The data for carbamylation of the total proteins from the skin samples Is shown in Table 3. The highest level of carbamylation was found in two skin samples incubated with growth medium supplemented with 4 mg/ml urea. The lowest level of carmamylation was found in the skin samples incubated with growth medium supplemented with both urea 4 mg/ml and the 2% amino acid creme, but the level of carbamylation from these skin samples was probably not statistical different from that seen in the control samples.

Combined Outcome of Examples 3 and 4

In example 3 the RHE samples was exposed to calculated real life conditions using histidine as an example of a nucleophile. All exposures were made on top of the skin samples. Carbamylation of proteins could be demonstrated within 6 days after exposure to urea concentrations calculated to be present in dialysis patients. Addition of 0.5% histidine, a concentration similar to the one present in NMF, prevented this carbamylation. The samples exposed to the commercial creams containing 5% and 10% urea developed hydration (as expected) of the stratum corneum (FIGS. 2 and 3) and the highest degree of protein carbamylation (table 2).

In example 4 the maximum tolerable exposure concentrations was tested, which is relevant for uremic pruritus as well as diaper dermatitis and urostomia dermatitis. The test was conducted in the RHE system. Further a cream containing 3 nucleophiles (amino acids) in a total concentration of 2% was tested. Urea was added in a concentration 8 times higher than in the average dialysis patient.

Figure 4:
FIG. 4 shows histological examinations of reconstructed human epidermis samples exposed to urea and a topically applied creme containing 2% amino acids.
Figure 4:
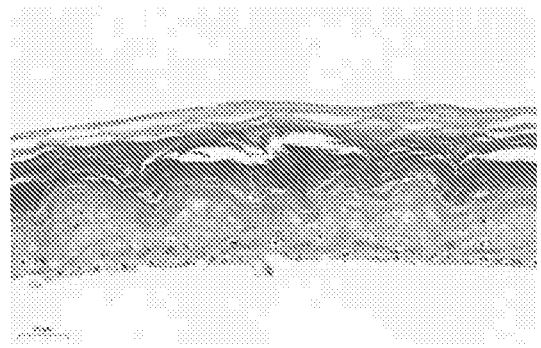
Figure 4:
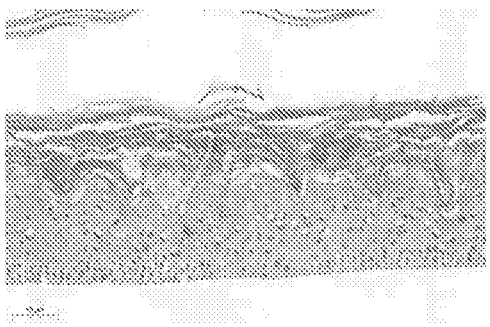

Application of the 2% amino acid cream caused the expected hydration of the RHE skin samples (FIG. 4). Protein analysis showed that the topically applied cream was able to prevent protein carbamylation during exaggerated urea concentrations exposures (table 3).

Example 5

In the following the preparation of representative formulations (I-VII) encompassed by the present invention are outlined.

I) Oil in Water Emulsion Cream Formula

| PHASE A | |
| --- | --- |
| Water | q.s. |
| Histidine | 0.50 |
| Citric acid (anhydrous) | 0.10 |
| Sodium citrate (dihydrate) | 0.17 |
| PHASE B | |
| Methylparaben | 0.15 |
| Glycerin | 8.00 |
| PHASE C | |
| Mineral oil | 26.00 |
| Petrolatum | 12.00 |
| Bees Wax | 3.00 |
| Sorbitan Stearate | 3.00 |
| Polysorbate 60 | 4.00 |
| Propylparaben | 0.15 |
| | 100.00 |

Premix phase A heating to 70° C.
Add phase B to phase A.
Heat phase C to 75° C.
Add phase C to phase A using high shear mixing.
Cool with mixing to 25° C.

II) Water-in-Oil Emulsion Cream Formula

| PHASE A | |
| --- | --- |
| Ethyl hexyl palmitate | 20.0 |
| Beeswax | 3.00 |
| Peg-7 hydrogenated castor oil | 1.00 |
| Polyglyceryl-3-polyricinoleate | 1.00 |
| PHASE B | |
| Magnesium sulfate | 1.00 |
| Histidine | 0.50 |
| Citric acid (anhydrous) | 0.10 |

| | |
|---|---|
| Sodium citrate (dihydrate) | 0.17 |
| Water | 73.23 |
| | 100.00 |

Method

Heat oil and water phases separately to 65-70
Add water phase (B) to oil phase (A) with stirring.
Stir to cool.

III) Gel Formula

| Ingredient | % |
|---|---|
| Glycerol | 3.00 |
| 2 Pyrrolidone 5 carboxylic acid (Na salt) | 0.50 |
| Histidine | 0.50 |
| Carbomer (Ultrez 10) | 0.80 |
| Citric acid | 0.10 |
| Sodium benzoate | 0.20 |
| Sodium hyalauronate | 0.05 |
| Sodium hydroxide (20% solution) | q.s (to pH 5.5) |
| Water | q.s. |
| | 100.00 |

Method

In first vessel (A) dissolve sodium hyalauronate in 50% of the water. Once dissolved add the glycerol, 2-pyrrolidone-5-carboxylic acid (sodium salt), citric acid and histidine. In a second vessel (B) disperse with suitable stirring the carbomer into 30% of the water. In a third vessel (C) dissolve the sodium benzoate in 5% water. Add the contents of vessel A into vessel B with stirring then add the contents of vessel C. Adjust the pH with Sodium hydroxide if required and then add water q.s.

IV) PEG Based Anhydrous Ointment Formula

| | |
|---|---|
| Oleic acid | 5.00 |
| Butylated hydroxyanisole | 0.10 |
| PEG 4000 | 25.00 |
| Histidine | 0.50 |
| PEG 400 | 69.40 |
| | 100.00 |

Method

Combine and heat oleic acid and butylated hydroxyanisole oil 65-70° C. with suitable stirring in vessel A. Combine and heat PEG 4000, histidine and PEG 400 to 65-70° C. with suitable stirring in vessel B. Add contents of vessel A into vessel B with high shear mixing for five minutes. Allow to cool to room temperature with moderate stirring.

V) Anhydrous Ointment Formula

| | |
|---|---|
| Cetyl palmitate | 5.00 |
| Diethyl sebacate | 8.00 |
| Squalane | 5.00 |
| Propylene glycol | 5.00 |
| Histidine | 0.50 |
| Vaseline | 76.50 |
| | 100.00 |

Method

Combine and heat propylene glycol and histidine 65-70° C. with suitable stirring in vessel A. Combine and remaining components to 65-70° C. with suitable stirring in vessel B. Add contents of vessel A into vessel B with high shear mixing for five minutes. Allow to cool to room temperature with moderate stirring.

VI) Shampoo Formula

| | |
|---|---|
| Sodium lauryl ether sulfate | 7.00 |
| Tetrasodium EDTA | 0.14 |
| Citric acid (anhydrous) | 1.11 |
| Cocamide monoethanolamine | 1.00 |
| Sodium lauryl sulfate | 7.00 |
| Cocoamidopropyl betaine | 2.00 |
| Sodium chloride | 0.70 |
| Water | q.s. |
| | 100.00 |

Method

Combine all ingredients with moderate stirring, minimizing foaming.

VII) Water-in-Oil Emulsion Cream Formula

| Ingredient | % |
|---|---|
| Versagel M200 (Mineral oil (and) ethylene/propylene/styrene copolymer (and) butylene/ethylene/styrene copolymer) | 8.58 |
| Isostearyl isostearate (ISIS) | 12.87 |
| Arlamol HD (isohexadecane) | 4.29 |
| Dimethicone 350 cst | 3.96 |
| Glycerol | 3.00 |
| Laureth 4 | 0.30 |
| 2 Pyrrolidone 5 carboxylic acid (Na salt) | 0.50 |
| L-Histidine | 0.50 |
| Carbomer (Ultrez 10) | 0.80 |
| L-Arginine | 0.75 |
| L-Lysine hydrochloride | 0.70 |
| Citric acid | 0.10 |
| Phenoxyethanol | 1.00 |
| Polysorbate 20 | 0.075 |
| Sodium hyalauronate | 0.05 |
| Sodium hydroxide (20% solution) | q.s (~0.70) |
| Water | q.s. (~62.33) |
| | 100.00 |

In a suitable vessel (A) combine the Versagel, Isostearyl isostearate, Arlamol HD and 0.26% laureth 4 with suitable mixing. In a second vessel (B) combine the dimethicone and 0.04% laureth 4 with suitable mixing. In a third vessel (C) mix the polysorbate 20 with 7.425% water. With moderate mixing slowly add first the contents of vessel A and then the contents of vessel B into vessel C. In a fourth vessel (D) combine the glycerol, 2-pyrrolidone-5-carboxylic acid (sodium salt), citric acid, L-histidine, L-arginine, L-lysine hydrochloride, sodium hyalauronate, phenoxyethanol and 37.85% water. In a fifth vessel (E) combine the carbomer and 13.50% water. Once fully dispersed and hydrated add with stirring the contents of vessel E into vessel C, then add the contents of vessel D. Adjust the pH (if required) using the sodium hydroxide and then make up to quantity with the remaining water.

REFERENCES

1 Fitzpatricks. Dermatology in general medicine. Eds. Freedberg I M et al. Six eds 2003, p 400.
2 Harrisons principles of internal medicine. Eds. Kasper et al 16th eds 2005. Chronic renal failure p 1653.
3 Fitzpatricks. Dermatology in general medicine. Eds. Freedberg I M et al six eds. 2003, p 103.

4 Al-Tamer Y Y, Hadi E A, al Badrani I I. Ural. Res. 1997; 25:337-40.
5 Fitzpatricks. Dermatology in general medicine. Eds. Freedberg I M et al. Six eds 2003, p 109.
6 Kezic S. Functions of filaggrin and its metabolites. In Flaggrin. Eds Thyssen J P and Maibach H I. 2014; p 3-9.
7 Kezic S, O'Regan G M, YanN et al. Levels of filaggrin degradation products are influenced by both filaggrin genotype and atopic dermatitis severity. Allergy. 2011; 66:934-940.
8 Nozaki Y and Tanford C. The solubility of amino acids and related compounds in aqueous urea solutions. J. Biol. Chem. 1963; 238:4074-4081.
9 Stark G. R and Smyth D. G. The use of cyanate for the determination of NH2-terminal residues in proteins. J. Biol. Chem. 1963, 238:214-226
10 Schmid-Wendtner M H and Korting H C, Skin Pharmacol. Physiol. 2006: 19:296-302
11 Rippke et al, Am. J. Clin. Dermatol. 2004; 5:217-23
12 Mauro et al, Arch. Dermatol. Res. 1998; 290: 215-22
13 Moss E et al. In situ metabolism of chinamyl alcohol in reconstructed human epidermis: New insights into the activation of this fragrance sensitizer. Chem. Res. Toxicol. 2016; 29: 1172-8.
14 Bandier J et al. Quantification of epidermal filaggrin in human skin and its response to skin irritation. J. Invest Dermatol. 2015; 136:1519-29.
15 G. R. Stark. Reactions of Cyanate with Functional Groups of Proteins. III. Reactions with Amino and Carboxyl Groups. Biochemistry 1965; 4: 1030-1036

The invention claimed is:

1. A method for treating itchy dry skin caused by urea, the method comprising applying a topical formulation to the itchy dry skin, the topical formulation comprising a nucleophile with a concentration of the nucleophile ranging between 0.001 mg/cm² and 5 mg/cm² skin surface.

2. The method according to claim 1, wherein the itchy dry skin caused by urea is selected from uremic pruritus, urostomi dermatitis, incontinence dermatitis, and diaper dermatitis.

3. The method according to claim 1, wherein the nucleophile is histidine and/or the derivative thereof.

4. The method according to claim 1, wherein the formulation further comprises pyrrolidone carboxylic acid.

5. The method according to claim 1, wherein the concentration of the nucleophile is between 0.003 mg/cm² and 1 mg/cm² skin surface.

6. The method according to claim 1, wherein the concentration of the nucleophile is between 0.005 mg/cm² and 0.5 mg/cm² skin surface.

7. The method according to claim 1, wherein the nucleophile is histidine and/or a derivative thereof, and is the only active ingredient in the topical formulation.

8. The method according to claim 1, wherein the method comprises treating pruritus in aging skin of elderly people.

9. The method according to claim 1, wherein the method comprises treating itchy dry skin in filaggrin defective patients.

10. The method according to claim 1, wherein the nucleophile is a nucleophilic amino acid, a peptide, or a derivative thereof.

11. The method according to claim 10, wherein the nucleophile is a nucleophilic amino acid comprising histidine.

12. The method according to claim 11, wherein the histidine comprises L-hisidine.

13. The method according to claim 10, wherein the nucleophile is selected from one or more of a histidine degradation product, a peptide of histidine, a peptide of histidine and one or more additional amino acids, and a pharmaceutically acceptable salt of histidine.

14. The method according to claim 10, wherein the topical formulation further comprises pyrrolidone carboxylic acid, or one or more of the amino acids glycylglycine, cysteine, arginine, and lysine.

15. The method according to claim 13, wherein the formulation comprises the pyrrolidone carboxylic acid, and the pyrrolidone carboxylic acid comprises sodium salt of the pyrrolidone carboxylic acid.

* * * * *